United States Patent
Hering et al.

(10) Patent No.: US 9,610,531 B2
(45) Date of Patent: Apr. 4, 2017

(54) WICK WETTING FOR WATER CONDENSATION SYSTEMS

(71) Applicant: Aerosol Dynamics Inc., Berkeley, CA (US)

(72) Inventors: Susanne Vera Hering, Berkeley, CA (US); Steven Russel Spielman, Oakland, CA (US); Gregory Stephen Lewis, Berkeley, CA (US); Nathan Michael Kreisberg, Richmond, CA (US)

(73) Assignee: AEROSOL DYNAMICS INC., Berkeley, CA (US)

( * ) Notice: Subject to any disclaimer, the term of this patent is extended or adjusted under 35 U.S.C. 154(b) by 245 days.

(21) Appl. No.: 14/043,455

(22) Filed: Oct. 1, 2013

(65) Prior Publication Data
US 2014/0033915 A1 Feb. 6, 2014

Related U.S. Application Data

(63) Continuation-in-part of application No. 13/218,393, filed on Aug. 25, 2011, now Pat. No. 8,801,838.

(Continued)

(51) Int. Cl.
*B01D 53/00* (2006.01)
*B01D 47/00* (2006.01)
(Continued)

(52) U.S. Cl.
CPC .......... *B01D 47/00* (2013.01); *B01D 5/0009* (2013.01); *B01D 53/1475* (2013.01);
(Continued)

(58) Field of Classification Search
CPC ....... G01M 15/102; F25J 3/08; F25J 2200/40; F25J 2200/70; G01N 15/06; G01N 15/065;
(Continued)

(56) References Cited

U.S. PATENT DOCUMENTS 2,042,095 A 5/1936 Grant, Jr.
2,684,008 A 7/1954 Vonnegut
(Continued)

FOREIGN PATENT DOCUMENTS

DE 4008348 A1 9/1991
EP 0462413 A2 12/1991
(Continued)

OTHER PUBLICATIONS

Notification of Transmittal of the International Search Report and the Written Opinion, mailed Jan. 16, 2014, in International Patent Application No. PCT/US2013/063082 filed Oct. 2, 2013.
(Continued)

*Primary Examiner* — Dung H Bui
(74) *Attorney, Agent, or Firm* — Vierra Magen Marcus LLP

(57) ABSTRACT

A system and method for particle enlargement with continuously wetted wicks includes a container into which a flow of particle-laden air is introduced in a laminar manner through an inlet and to an outlet. The container has a first section, a second section and a third section though which the particle-laden air flows between the inlet and the outlet. The temperature of the second section is warmer than that of the first section at the inlet and the third section at the outlet. In one embodiment, a continuous wick spanning an interior wall of the first second, second section and third section, said wick being capable of internally transporting liquid water along its length is provided.

19 Claims, 11 Drawing Sheets

Related U.S. Application Data

(60) Provisional application No. 61/709,084, filed on Oct. 2, 2012, provisional application No. 61/402,348, filed on Aug. 27, 2010.

(51) Int. Cl.

| | |
|---|---|
| *B01D 53/14* | (2006.01) |
| *B01D 53/18* | (2006.01) |
| *B01D 5/00* | (2006.01) |
| *G01M 15/10* | (2006.01) |
| *F25J 3/08* | (2006.01) |
| *G01N 15/06* | (2006.01) |
| *G01N 15/14* | (2006.01) |
| *G01N 15/00* | (2006.01) |

(52) U.S. Cl.
CPC ........... *B01D 53/18* (2013.01); *G01N 15/065* (2013.01); *F25J 3/08* (2013.01); *F25J 2200/70* (2013.01); *G01M 15/102* (2013.01); *G01N 15/06* (2013.01); *G01N 2015/0038* (2013.01); *G01N 2015/1481* (2013.01)

(58) Field of Classification Search
CPC ... G01N 2015/0038; G01N 2015/1481; B01D 47/00; B01D 5/0009
USPC .... 95/228, 288, 149, 227; 96/243, 288, 322, 96/413; 73/28.05, 28.01, 28.04, 31.02, 73/31.03, 863.12, 863.21, 23.31; 62/617, 62/640, 657; 356/37, 339
See application file for complete search history.

(56) References Cited

U.S. PATENT DOCUMENTS

| | | | |
|---|---|---|---|
| 2,721,495 A | 10/1955 | Schaefer | |
| 3,011,387 A | 12/1961 | Johnson | |
| 3,011,390 A | 12/1961 | Van Luik, Jr. | |
| 3,037,421 A | 6/1962 | Bigelow et al. | |
| 3,592,546 A | 7/1971 | Gussman | |
| 3,632,210 A | 1/1972 | Rich | |
| 3,694,085 A | 9/1972 | Rich | |
| 3,738,751 A | 6/1973 | Rich | |
| 3,806,248 A | 4/1974 | Sinclair | |
| 3,890,046 A | 6/1975 | Hart et al. | |
| 4,293,217 A | 10/1981 | Bird, Jr. et al. | |
| 4,449,816 A | 5/1984 | Kohsaka et al. | |
| 4,761,074 A | 8/1988 | Kohsaka et al. | |
| 4,790,650 A | 12/1988 | Keady | |
| 4,792,199 A | 12/1988 | Borden | |
| 4,868,398 A | 9/1989 | Mulcey et al. | |
| 4,950,073 A | 8/1990 | Sommer | |
| 4,967,187 A | 10/1990 | Dumas et al. | |
| 5,011,281 A | 4/1991 | Harris | |
| 5,026,155 A | 6/1991 | Ockovic et al. | |
| 5,098,657 A | 3/1992 | Blackford et al. | |
| 5,118,959 A | 6/1992 | Caldow et al. | |
| 5,176,723 A | 1/1993 | Liu et al. | |
| 5,239,356 A | 8/1993 | Hollander et al. | |
| 5,278,626 A | 1/1994 | Poole et al. | |
| 5,519,490 A | 5/1996 | Nakata et al. | |
| 5,659,388 A | 8/1997 | Scheer et al. | |
| 5,675,405 A | 10/1997 | Schildmeyer et al. | |
| 5,872,622 A | 2/1999 | Schildmeyer et al. | |
| 5,903,338 A | 5/1999 | Mavliev et al. | |
| 6,330,060 B1 | 12/2001 | Flagan et al. | |
| 6,469,780 B1 | 10/2002 | McDermott et al. | |
| 6,498,641 B1 | 12/2002 | Schildmeyer | |
| 6,529,272 B2 | 3/2003 | Flagan et al. | |
| 6,567,157 B1 | 5/2003 | Flagan et al. | |
| 6,712,881 B2 | 3/2004 | Hering et al. | |
| 6,829,044 B2 | 12/2004 | Liu | |
| 6,980,284 B2 | 12/2005 | Ahn et al. | |
| 7,298,486 B2 | 11/2007 | Wang et al. | |
| 7,719,683 B2 | 5/2010 | Ahn | |
| 7,724,368 B2 | 5/2010 | Ahn | |
| 7,736,421 B2 | 6/2010 | Hering et al. | |
| 7,828,273 B2 | 11/2010 | Molter et al. | |
| 7,988,135 B2 | 8/2011 | Molter et al. | |
| 8,072,598 B2 | 12/2011 | Ahn | |
| 2003/0082825 A1 | 5/2003 | Lee et al. | |
| 2004/0020362 A1 | 2/2004 | Hering et al. | |
| 2006/0126056 A1 | 6/2006 | Roberts et al. | |
| 2006/0146327 A1* | 7/2006 | Wang | G01N 15/0266 356/338 |
| 2006/0156791 A1 | 7/2006 | Tikkanen et al. | |
| 2008/0041138 A1 | 2/2008 | Marra | |
| 2008/0083274 A1 | 4/2008 | Hering et al. | |
| 2008/0137065 A1 | 6/2008 | Oberreit et al. | |
| 2008/0144003 A1* | 6/2008 | Blackford | G01F 1/661 356/37 |
| 2010/0180666 A1 | 7/2010 | Huetter et al. | |
| 2011/0095095 A1 | 4/2011 | Hering et al. | |
| 2012/0048112 A1 | 3/2012 | Hering et al. | |
| 2014/0029154 A1 | 1/2014 | Hering et al. | |

FOREIGN PATENT DOCUMENTS

| | | |
|---|---|---|
| EP | 2208983 A2 | 7/2010 |
| WO | WO8908245 A1 | 9/1989 |
| WO | 2008058182 A2 | 5/2008 |

OTHER PUBLICATIONS

International Preliminary Report on Patentability, mailed Apr. 16, 2015, in International Patent Application No. PCT/US2013/063082 filed Oct. 2, 2013.

International Preliminary Report on Patentability, mailed Apr. 16, 2015, in International Patent Application No. PCT/US2013/063076 filed Oct. 2, 2013.

Notification of Transmittal of the International Search Report and the Written Opinion, mailed Apr. 25, 2014, in International Patent Application No. PCT/US2013/063076 filed Oct. 2, 2013.

Office Action dated Jun. 10, 2015, in U.S. Appl. No. 14/043,662, filed Oct. 1, 2013.

Leaitch, R., et al., "The Diffusion Tube: A Cloud Condensation Nucleus Counter for Use Below 0.3% Supersaturation," Journal of Aerosol Science., vol. 13, No. 4, 1982, 23 pages.

Choi, Youngjoo, et al., "An improved method for chargin submicron and nanoparticles with uniform charging performace," Aerosol Science and Technology, vol. 41, Issue 3, pp. 259-265, Jan. 2007.

Han, B.W., et al., "Enhanced unipolar charging of concentraion-enriched particles using water-based condensational growth," Journal of Aerosol Science, vol. 39, Issue 9, pp. 770-784, Sep. 2008.

Hering, Susanne V., et al., "A Method for Particle Size Amplification by Water Condensation in a Laminar, Thermally Diffusive Flow," Aerosol Science and Technology, 39: 428-436, Mar. 2005, 9 pages.

Hering, Susanne V., et al., "A Laminar-Flow, Water-Based Condensation Particle Counter (WCPC)," Aerosol Science and Technology, 39: 659-672, Apr. 2005, 14 pages.

Stolzenburg, Mark R., et al., "An Ultrafine Aerosol Condensation Nucleus Counter," Aerosol Science and Technology, 14:48-65, Jan. 1991, 19 pages.

Invitation to Pay Additional Fees and Communication Relating to the Results of the Partial International Search dated Nov. 4, 2011, in International Patent Application No. PCT/US2011/049391 filed Aug. 26, 2011.

Seager, Spencer L., et al., "Temperature Dependence of Gas and Vapor Diffusion Coeeficients," Journal of Chemical & Engineering Data, vol. 8, No. 2, Apr. 1, 2963, pp. 168-169.

English Abstract of European Publication No. EP 0462413 published Dec. 27, 1991.

English Abstract of European Publication No. EP 2208983 published Jul. 21, 2010.

International Search Report dated Jan. 18, 2012, International Application No. PCT/US2011/049391.

(56) References Cited

OTHER PUBLICATIONS

Office Action dated Apr. 9, 2013, U.S. Appl. No. 13/218,393, filed Aug. 25, 2011.
Response to Office Action dated Jul. 9, 2013, U.S. Appl. No. 13/218,393, filed Aug. 25, 2011.
Office Action dated Aug. 30, 2013, U.S. Appl. No. 13/218,393, filed Aug. 25, 2011.
Kim, D. S., et al., "Control of nanoparticle charge via condensation magnification," Journal of Aerosol Science, vol. 37, Issue 12, pp. 1876-1882, Dec. 2006.
Suh, J. B., et al., "A method for enhanced charging of nanoparticles via condensation magnification," Journal of Aerosol Science, vol. 36, Issue 10, pp. 1183-1193, Oct. 2005.
Amendment dated Mar. 7, 2016, in U.S. Appl. No. 14/043,662, filed Oct. 1, 2013.
Amendment dated Sep. 10, 2015, in U.S. Appl. No. 14/043,662, filed Oct. 1, 2013.
Office Action dated Nov. 6, 2015, in U.S. Appl. No. 14/043,662, filed Oct. 1, 2013.
McMurry, Peter H., "The History of Condensation Nucleus Counters," Aerosol Science and Technology, Oct. 2000, 26 pages.

\* cited by examiner

WICK WETTING FOR WATER CONDENSATION SYSTEMS

CLAIM OF PRIORITY

This application is a continuation in part of U.S. patent application Ser. No. 13/218,393 filed on Aug. 25, 2011 entitled, "ADVANCED LAMINAR FLOW WATER CONDENSATION TECHNOLOGY FOR ULTRAFINE PARTICLES", which claims priority to U.S. Provisional Application No. 61/402,348 filed Aug. 27, 2010, which applications are hereby incorporated by reference in their entirety.

This application claims priority to U.S. Provisional Application Ser. No. 61/709,084 filed Oct. 2, 2012, inventors, Susanne V. Hering, Steven R. Spielman, Gregory S. Lewis and Nathan M. Kreisberg, which application is hereby incorporated by reference in its entirety.

GOVERNMENT LICENSE RIGHTS

This technology was made with government support under Grant No. RC3ES19081 from the National Institute of Environmental Health, and DE-SC0006312 and DE-SC00469 from the U.S. Department of Energy. The government has certain rights in the technology.

BACKGROUND

Many applications have utilized the condensational growth of airborne particles to enable their measurement or collection. For ultrafine particles the initiation of this growth requires the creation of a region of vapor supersaturation. U.S. Pat. No. 6,712,881 describes a method to create this supersaturation in a laminar flow, wherein a flow passes through a wet-walled tube, or other container, the second portion of which is warmer than the first portion. U.S. patent application Ser. No. 13/218,393 describes a different method in which the temperature profile of the wetted walls has a cold section, a warm section, and a final cold section. These laminar flow systems that create water vapor supersaturation have come to be known as condensation growth tubes These condensation growth tubes work by exposing an air flow to wetted surfaces at different temperatures. The wetted surface is commonly implemented as a wick, which is a porous medium that will readily draw water into its pores via capillary action. During operation of these condensation systems, water evaporates from the warm portion of the wick, and thus the wick must be continually supplied with more water. To accomplish this, various wetting methods have been used. In some systems, water pumped to the outside of a cylindrical wick is drawn to the inside by capillary action. The excess water cascades down the length of the tube via gravity. Other systems use an internal reservoir wetting system, wherein the bottom end of the wick is submerged in a reservoir of water.

Disadvantages of this prior art are the complications in the water handling, risk of flooding and sensitivity to being tipped. Protrusions into the flow channel, as required for the reservoir wetting system, are a problem for some applications.

FIG. 1 shows one prior art system for passive wetting of a wick 100. A dike 150 (sometimes called the "standpipe") having a base 155 is a necessary barrier to prevent water 140 from seeping under or through the wick 100 where it would drip into lower parts of the device. Water 140 is transported up the wick 100 by capillary action. An aluminum housing 110 provides structure and a good thermal connection to the heater or cooler 120. In the case of a wick that consumes water, a filling system 130 is required, comprised of a water level sensor controlling a pump or valve, and an air vent 125. The air vent 125 communicates with the inlet flow to provide pressure equalization between the head space of the water reservoir and the flow. The system ensures the reservoir 145 neither fills above the upper edge of the dike 150, nor goes completely empty. In the case of a cold wick where water vapor condenses, the system must discard water.

SUMMARY

Technology is presented which provides passive wetting of the wicks which may form the wetted walls of the laminar flow water condensation growth systems. In one aspect, a self-sustaining wick relies on capillary action of the wick material to transport water from colder regions where water vapor condenses onto the wick surface to warmer sections where it evaporates. This approach allows extended operation without a water reservoir, and is insensitive to being tipped. In another aspect, a siphoned wick uses a siphon-like method to maintain a water-filled gap behind the wick on a side of the wick opposite the air flow. This approach may be supplemented with active pumping to accommodate large systems.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Figure 1:
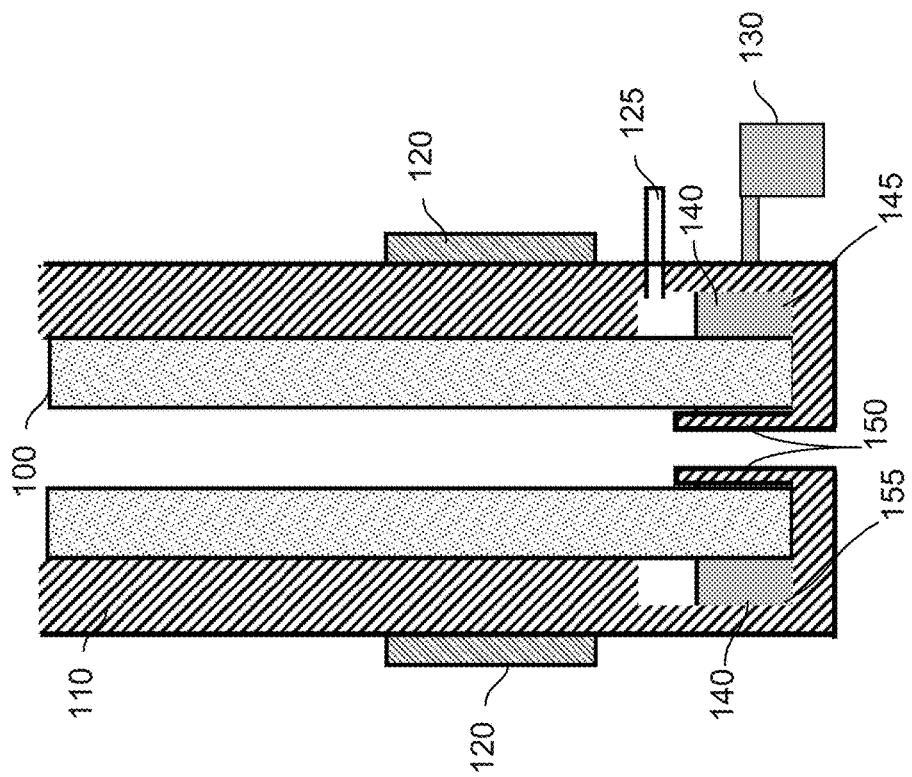
FIG. 1 depicts a prior art, capillary action wicking system using water from a small reservoir drawing into a porous wick.

Technology is presented which provides novel systems and methods of providing wetted walls of water condensation systems used to produce water vapor supersaturation in a flow of air or other gas. In one aspect, a self-sustaining wick relies on capillary action of the wick material to transport water from colder regions where water vapor condenses onto the wick surface to warmer sections where it evaporates. In another aspect, a siphoned wick uses a siphon-like method to maintain a water-filled gap behind the wick on a side of the wick opposite the air flow. This approach may be supplemented with active pumping to accommodate large systems. The prior art utilizes an internal reservoir for wetting of the wick, as illustrated in FIG. 1. This requires a dike that protrudes into the flow, a problem for some applications. Additionally, it requires mostly upright operation so that water in the internal reservoir does not spill into the air flow. It also requires a vent to equalize the pressure in the head space of the internal and external reservoirs with the pressure of the flow inside the tube. If these conditions are not met, the system can flood. The self-sustaining wick of this technology is designed to overcome these limitations.

Figure 2:
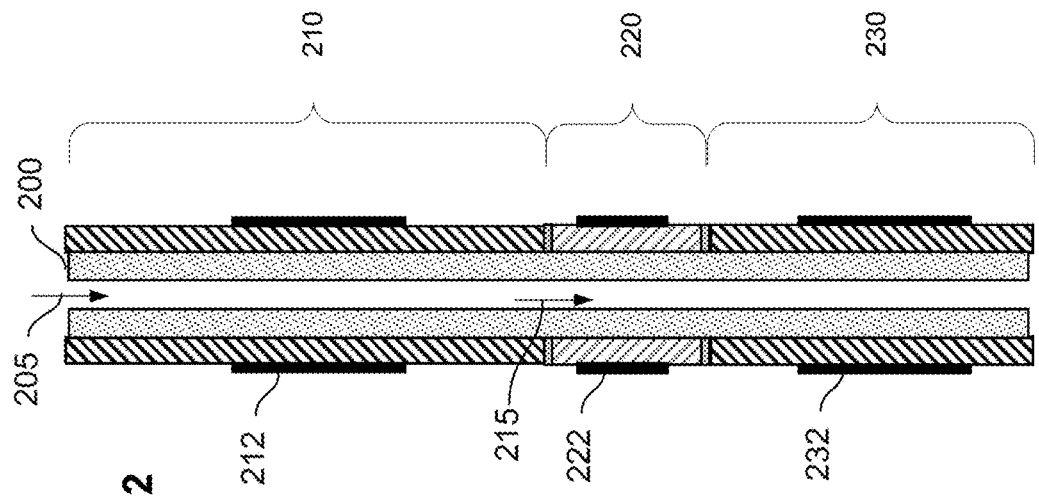
FIG. 2 illustrates a first embodiment of wicking technology comprising a self-sustaining wick.

FIG. 2 illustrates a self-sustaining wick 200 providing a wick spanning several temperature zones (210, 220, 230), wherein the downstream colder section 230 recovers water vapor released from the warm section 220, and this water is returned to the warmed section by capillary action, where it evaporates to create supersaturation in the cooler flow at 215 entering from the upstream cold section 210. Additionally, if the temperature of the first stage 210 is lower than the dew point of the sample air flow, water from the air flow will condense onto the wick in this first stage and will be transported to the warmed section by capillary action.

As shown in FIG. 2, a self-sustaining wick uses a three stage growth system, with a single, wetted wick 200 spanning all three stages. The first stage 210 is a "conditioner." The second stage 220 and third stage 230, referred to as the "initiator" and "equilibrator", respectively, form a two-part condenser, as described in U.S. patent application Ser. No. 13/218,393. The conditioner 210 including cooler 212 is generally operated with slightly cooled walls, and is used to bring the flow 205 to near the temperature of the conditioner walls, with a relative humidity near 100%. The second, "initiator" stage 220 includes heater 222 and has walls which are maintained warmer than that of the conditioner 210. The third, equilibrator stage 230 includes cooler 232 and is operated cooler than the initiator stage 220. As the cooler flow from the conditioner enters the warm, wet walled initiator section, water vapor diffuses from the walls into the cooler flow. Likewise the flow slowly warms. Yet, because of its high diffusion constant relative to the thermal diffusivity of air, water vapor diffuses more quickly. As a result, the flow becomes supersaturated, with its peak supersaturation along the centerline of the flow. With the two-stage condenser 240, this region of water vapor supersaturation forms in the initiator section, and extends into the equilibrator section 230.

This water vapor supersaturation activates the condensational growth on small particles, which because of their surface curvature and associated surface tension have equilibrium vapor pressures that are greater than that over a flat surface of the same composition. As described by the Kelvin relation, the required equilibrium vapor pressure is higher for smaller particles, increasing as the inverse of the particle diameter. The warm wetted wall of the initiator provides the water vapor that creates the supersaturation. Further downstream, in the equilibrator, much of this water vapor from the supersaturated flow condenses onto the wick, reducing the water vapor content, as reflected in the reduction of the dew point. However, the flow remains supersaturated, and particles continue to grow via condensation, producing droplets that may be detected optically, or collected by inertial means. As shown in U.S. patent application Ser. No. 13/218,393, the equilibrator of this configuration reduces the dew point and temperature of the flow, with minimal effect on extent of vapor supersaturation.

With this the self-sustaining wick 200, evaporated water from the wick in the warm initiator section 220 is carried by the flow into the equilibrator section 230. The colder walls of the equilibrator 230 cause much of the water vapor to condense onto the wick 200. This recovered water, now in liquid state, is then transported back through the wick to the warmed mid-section 220 via capillary action. The conditioner 210 may supply additional water to the initiator section 220 of the wick if the incoming sampled air has a dew point that is higher than the conditioner temperature.

When the entering flow has a dew point above about 10° C., as is often the case for summertime ambient conditions, then it is possible to set the temperature of the walls of the equilibrator such that the dew point of the flow exiting the system matches that at the inlet. Under these conditions the rate of water condensation onto the wick in the conditioner and equilibrator sections will match that rate of evaporation in the initiator section (as the water lost to the droplet formation is small). This provides a self-sustaining wick. If one starts with a fully wetted wick, and the dew point of the exiting flow is slightly higher than that of the entering flow, the system will still produce supersaturation and droplet growth needed for particle detection or capture, yet will operate for several days without needing to be replenished.

FIG. 3A illustrates an alternate configuration of a self-sustaining wick wherein the entering flow 305 passes through a temperature controlled humidifier 350. The system of FIG. 3A includes a conditioner stage 310, initiator stage 320 and equilibrator stage 330. Conditioner stage 310 includes a cooler 312. Initiator stage 320 includes a heater 322. Equilibrator stage 330 includes a cooler 332. A droplet collector or droplet detector 390 is positioned at the outlet 385 of the growth flow region.

The configuration of FIG. 3A does not require matching the exiting dew point to that of the entering flow. In this configuration, a temperature controlled humidifier 350 adjusts the dew point of the flow, entering the conditioner to match that which exits an equilibrator 330. Humidifier 350 can be a simple Nafion tube system such as those available commercially from Perma Pure LLC, Toms River N.J. This is a membrane system that provides humidification via chemical transport through the membrane, and without physical contact between the supply water and the flow. Thus the tube is spill-proof and completely tippable. This provides a means to balance the input and output dew points under conditions when the sample flow dew point is low, e.g. below 5° C. With this approach, the system of FIG. 3A can be operated for long period of time without addition of water, except as required for the inlet humidifier 350.

Optionally, a transport flow 365 and a secondary flow 355 may be provided, as shown, that can carry away excess condensate, so that longer periods of operation are possible. Typically, these flows may comprise 5% to 20% of the total flow 305. The transport flow 365 is extracted from the annular region surrounding the inlet tube 305B, before the flow 307 enters the conditioner stage 310. In addition to providing a means to carry away excess water, flow 365 helps to provide more efficient transport of ultrafine particles to inlet, as is often provided for condensation particle counters. At the opposite, downstream end of the growth tube, a secondary outlet flow 355 is provided that draws air from that portion of the flow 307 that is closest to the walls. This may be accomplished through use of a fluted design of the outlet nozzle 385 that provides passageway from the air flow channel to the secondary outlet chamber 356. Only the remaining portion of the flow 375 passes through the droplet detector or collector 390. The particles in the flow 375 are subject to measurement. Optionally a sponge or other absorbent material can be placed in the transport flow outlet chamber 360 to avoid spillage should the system be tipped during operation.

Figure 3A:
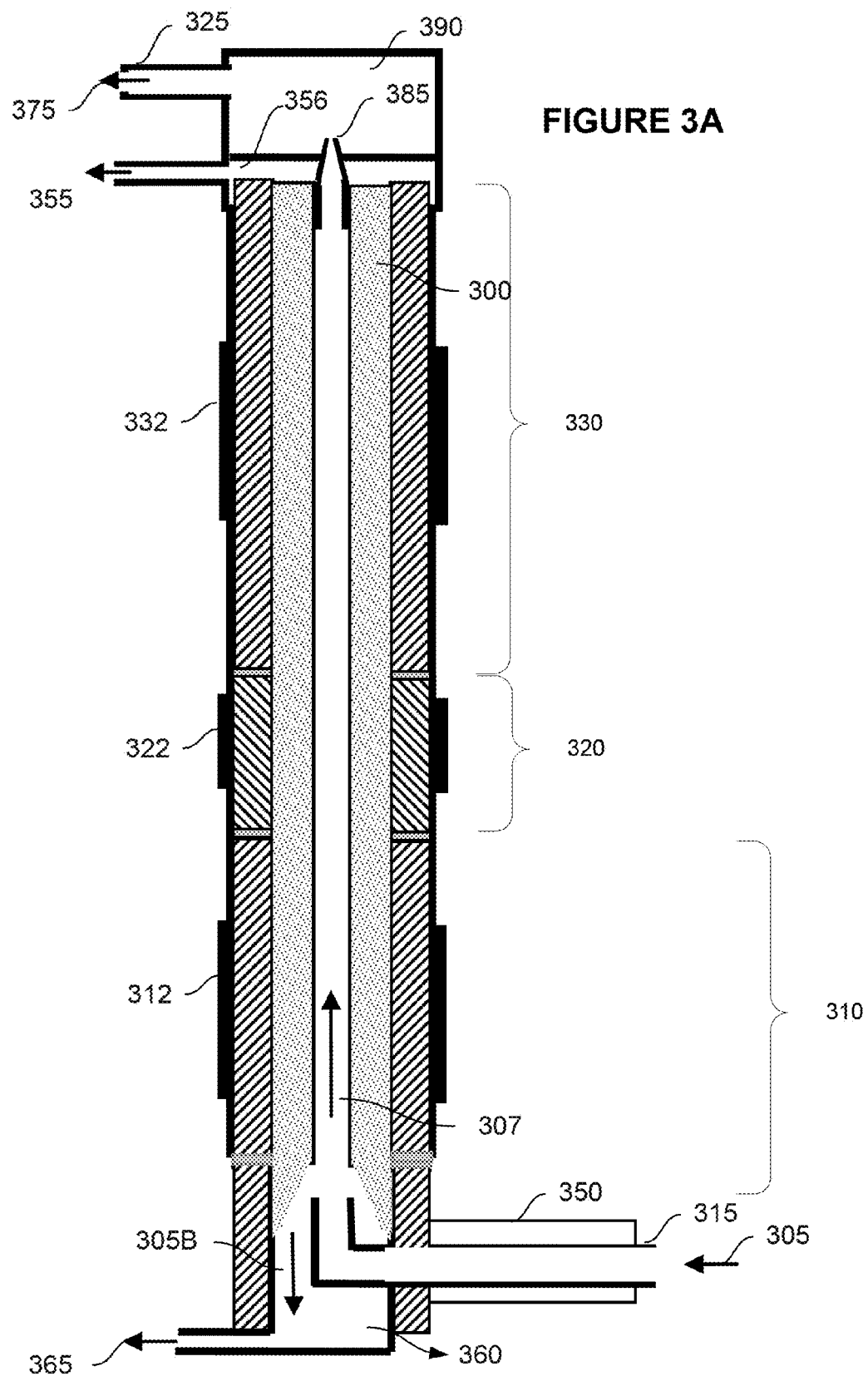
FIGS. 3A and 3B illustrates alternate configurations of the self-sustaining wick using a conditioner.
Figure 3B:
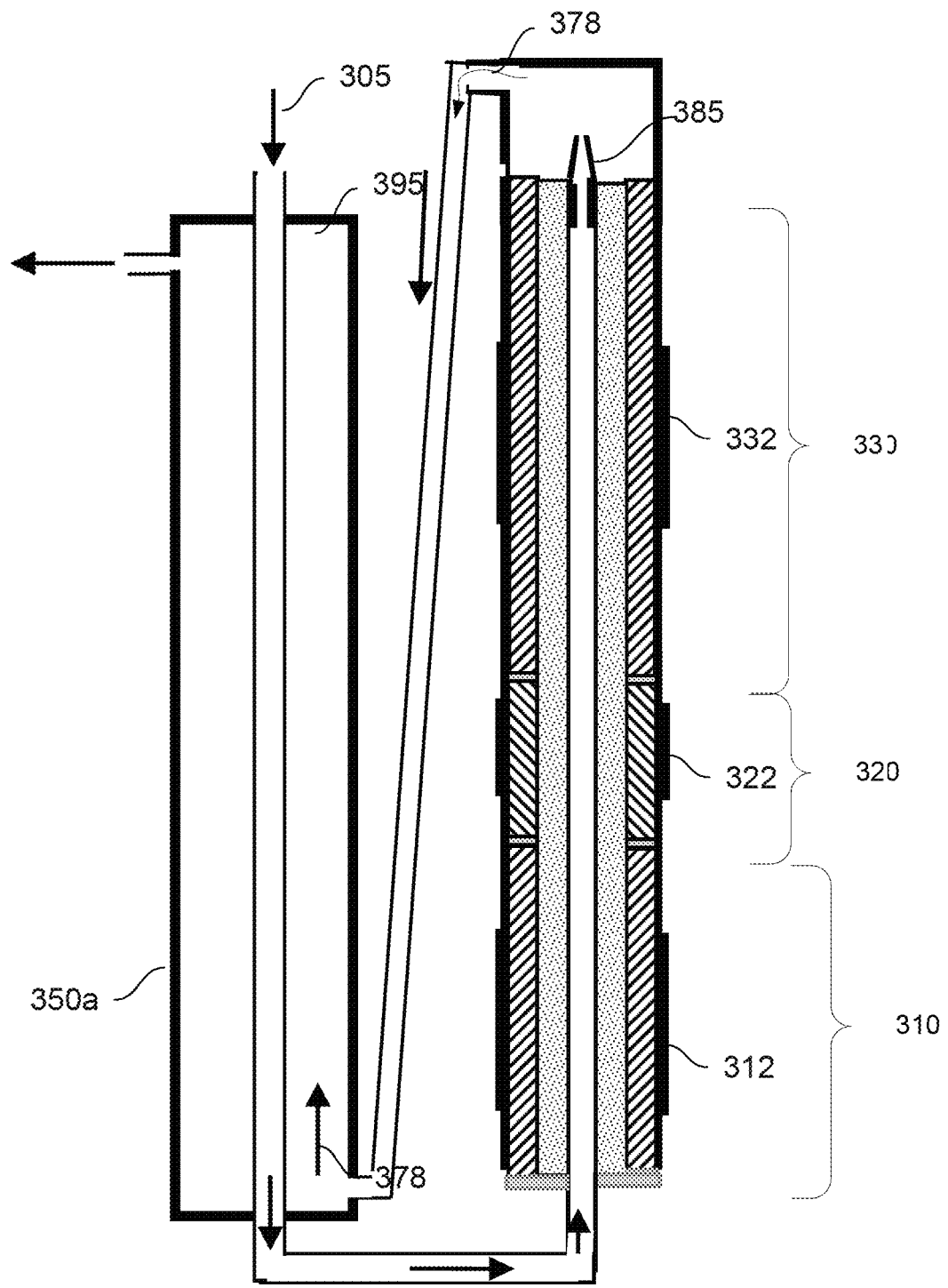

FIG. 3B shows an alternative use of the Nafion humidity exchange membrane 350 shown in FIG. 3A. The airflow 378 exiting the droplet detector or collector 385 is directed into the shell space 395 of the Nafion humidity conditioner 350A. This shell space is the region outside the Nafion tubes 383 through which the sample stream 305 flows. Due to the unique properties of the Nafion, which actively transports water molecules based on the difference in relative humidity across the Nafion membrane, water will be transferred in or out of the sample flow 305 so as to equalize the humidity of the two streams 305 and 378. In this way the inlet flow 305 is approximately conditioned to the same dew point as the exit flow 378. This provides a self-sustaining system that operates for long periods of time without the need to introduce additional water. This approach performs under a wide range of ambient relative humidity conditions. Because there are no water reservoirs, it is tolerant to motion.

To test this system, a condensation particle counter was constructed using components from the commercial condensation particle counter, the TSI Model 3783. A system using the conditioner, initiator and equilibrator was created with all three stages lined with a single, continuous wick. The wick was formed by rolling a sheet of Nylasorb™ filter media into a cylindrical tube measuring approximately 5 mm ID and 9 mm OD. The cooling of the conditioner and equilibrator walls was achieved by two sets of thermal electric devices (Peteltier type coolers) and heating was done using a film heater. The overall length of the system is 250 mm and the sample flow rate was generally controlled to 0.3 L/min. The droplets formed from this system were counted using the optics head and electronics from the TSI Model 3783. Results were compared to commercial bench top counters, the TSI Model 3787 and TSI Model 3788.

Figure 4:
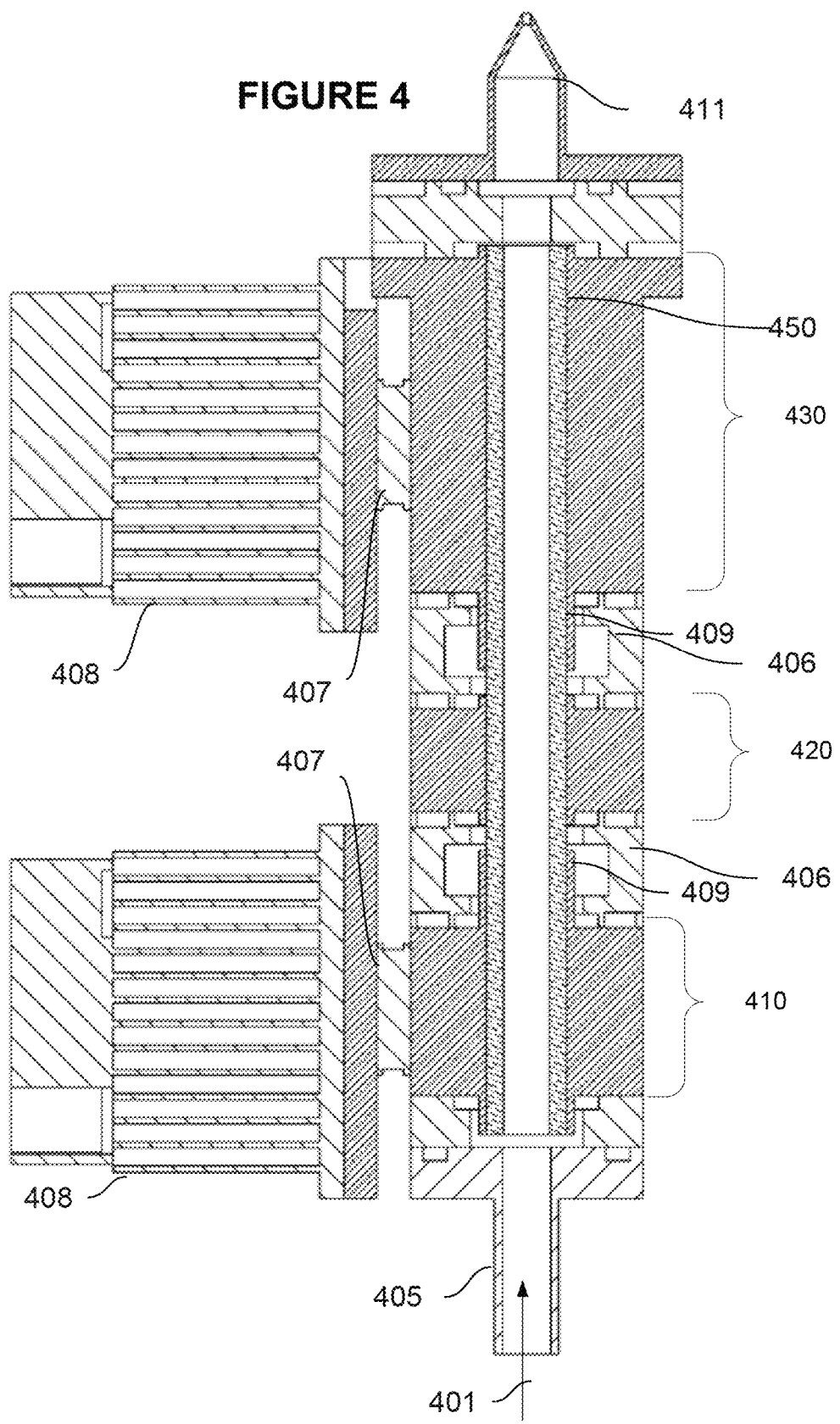
FIG. 4 depicts the mechanical construction of a system following the embodiment shown in FIG. 1.

FIG. 4 shows another embodiment of a system using a self-sustaining wick. This system has a cylindrical shape, and is designed to accommodate an air flow rate of 0.1-0.2 L/min. The air stream 401 that is being sampled enters at an inlet at 405, and passes through conditioning stage 410, initiator stage 420 and equilibrator stage 430. Insulation sections 406 thermally isolate these stages. A wick 450 formed by rolling a length of Nylasorb filter material spans all three sections. The flow exits through a nozzle 411 which may be coupled to an optics head for particle counting, or to an impaction stage for particle collection. The temperature of the conditioner stage is controlled by a thermoelectric device 407 which is coupled to cooling fins 408. A similar thermoelectric device and cooling fins are used to cool the conditioner stage. The initiator stage is heated by means of a cartridge heater, which is not shown in the drawing. The active lengths of the conditioner 410 and equilibrator 420 are lengthened by means of an foot 409 that extends under the insulator sections 406. The active lengths of the conditioner 410, initiator 420 and equilibrator 430 are 28 mm, 13 mm, and 42 mm respectively, separated by 2.5 mm long insulator sections. The inside diameter of the wick 450 is 5 mm. The overall length, including an optics head is 150 mm.

Figure 5A:
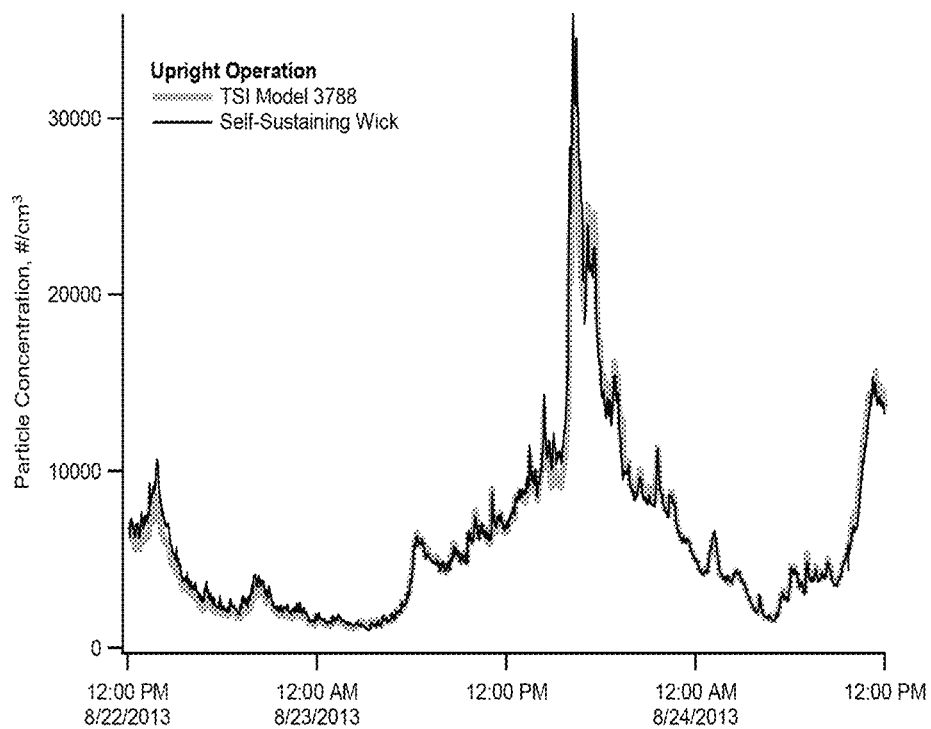
FIGS. 5A and 5B illustrate exemplary performance data for a self-sustaining wick employed as part of a condensation particle counter.
Figure 5B:
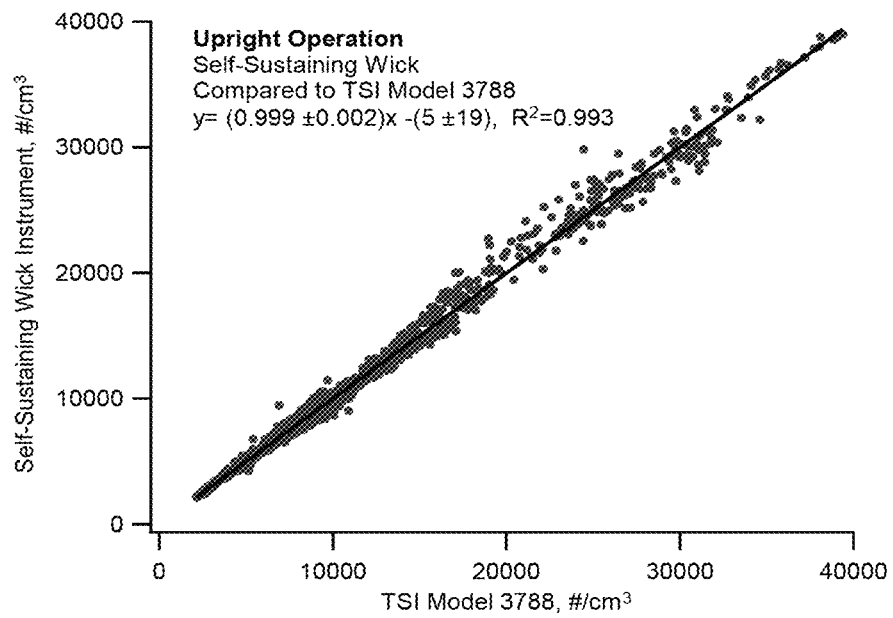

FIG. 5 shows data from the system of FIG. 3A without use of a humidifier, secondary or transport flows. The wick was wetted at the beginning of the tests, and then run without replenishment. The operating temperatures were around 5° C. for the conditioner, 45° C. for the initiator, and 12-15° C. for the equilibrator, and 45° C. for the optics head. Consistent operation was obtained for more than two weeks of continuous operation, until the test was stopped.

Figure 6A:
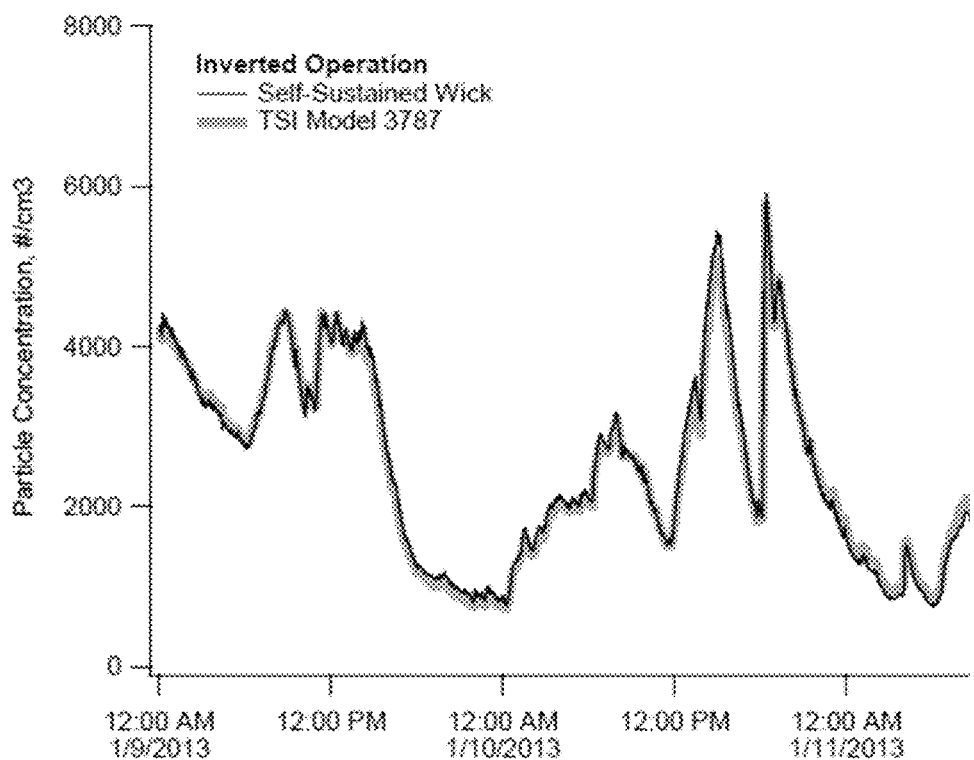
FIGS. 6A and 6B illustrate exemplary data for inverted operation of a condensation particle counter employing a self-sustaining wick.
Figure 6B:
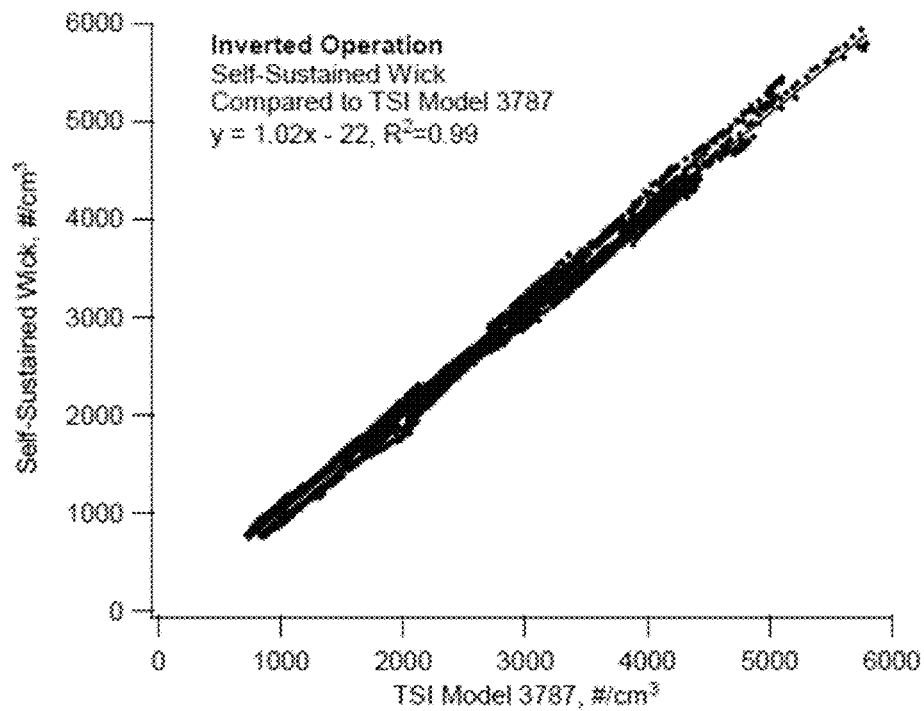
Figure 7A:
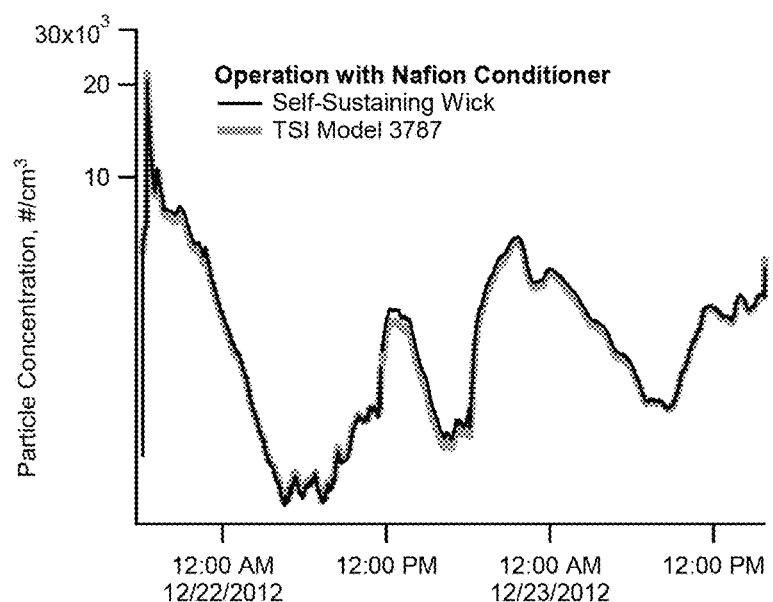
FIGS. 7A and 7B illustrate exemplary data for a self-sustaining wick, in a configuration that uses a humidity exchange membrane on the incoming flow.
Figure 7B:
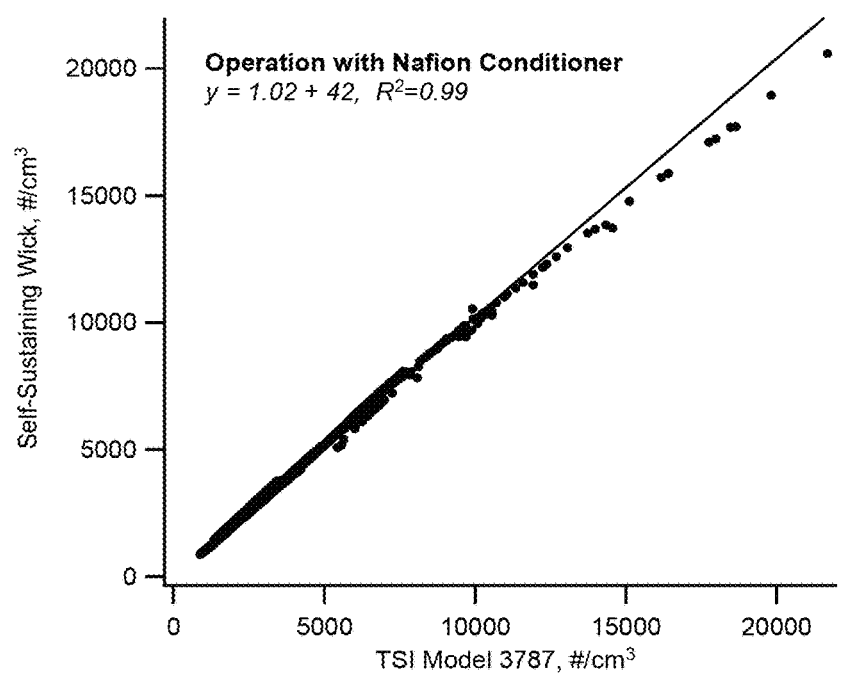
Figure 8:
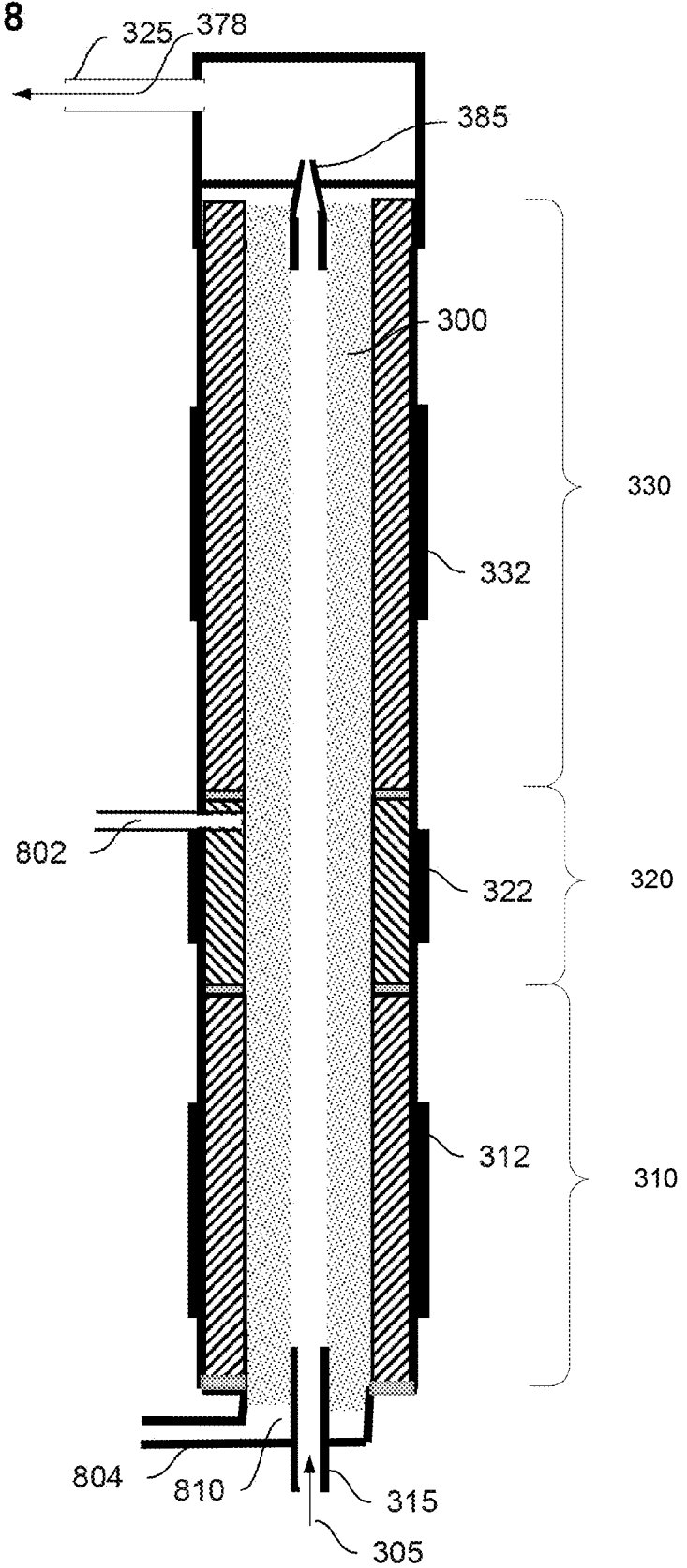
FIG. 8 illustrates an alternate configuration of a self-sustaining wick in which water is injected, and any overflow is removed, via secondary air flows.

FIG. 6 shows a similar test with inverted operation. For this data set a linear regression against the bench top counter gave a correlation coefficient of $R^2=0.99$, and a slope of 1.02. This 2% discrepancy is considered within the error of the flow measurement.

For sustained operation, it is advantageous that the input and output water content be well-balanced, or that there is a mechanism for removing excess water that may accumulate. Under extreme conditions of very dry, or very wet relative humidity, the system as configured in FIG. 2 may be used with a balancing component. In the case of sampling dry air, the equilibrator may not be able recover sufficient moisture to fully replenish the initiator portion of the wick. In the case of sampling extremely moist air, it is possible to flood the system from water vapor that is removed from the incoming air. Balancing improves operation under these extreme conditions.

Tests were conducted with the configuration of FIG. 3B, wherein the flow exiting the optics head is recirculated through the shell of a Nafion humidity conditioner. The Nafion is a non-permeable membrane material that transports water molecules from the high to low humidity side of the membrane via chemical reaction. For this application, a tube of the Nafion from Perma Pure, (Toms River, N.J.) was utilized. Prior to entering the conditioner, the sample flow is directed through this tube, while the sample flow exiting the optics head (or droplet collector) is directed in a counterflow direction through the she space surrounding the Nafion tube. This allows for exchange of water content between the two flows without otherwise mixing. This system was tested with laboratory air that was dried to 5-23% RH using a large diffusion dryer prior to entering the system. This approach provided more than one day of continuous operation, as shown by the data of FIG. 7. However, the good agreement with the bench top counter seen in the data of FIG. 7 is not observed when sampling directly from ambient air. We find that the Nafion preconditioner removes about 10% of the ambient particles, leading to a corresponding reduction in the values for the particle number concentration. These losses were not seen in FIG. 7 as the smaller particles that are lost in the Nafion system were already removed by the large dryer used upstream to create the low humidity for the tests.

For long-term operation, this self-sustaining wicking concept of FIG. 3A can be adapted to system in wherein a small amount of water is injected at the initiator stage, and excess water is removed with a secondary flow, as shown in FIG. 8. In the system of FIG. 8, like numbers represent like parts presented in the above discussion of FIG. 3A. In the system of FIG. 8, a water fill line 802 is provides a means to inject water onto the wick. The tube 810 which is inserted into the base of the wick is equipped with a slightly recessed lip 810 or fluted section which provide a passage way so that excess water that accumulates on the wick can be carried away by a secondary flow drawn through port 804. This secondary flow can be 5-10% of the total aerosol flow. The water injected can be programmed based on the incoming relative humidity and temperature measurement, such that the total water consumption is minimized. Experimental results show that at relative humidity conditions above about 40% RH at 20° C., with a equilibrator operated at 14° C., the water injection required is less than 5 μL/hour per L/min of sample flow. This approach, while requiring an upright orientation, provides robust operation over weeks of operation.

The self-sustaining wick offers a number of advantages over the prior art approach of FIG. 1. Long term operation without a water reservoir is provided. Elimination of the water reservoir also eliminates the need for pressure equalization, and eliminates water spillage. Overall the water handling is much simpler than in the prior art design of FIG. 1. Elimination of the water reservoir permits operation at multiple orientations. No dike or other object protruding into the flow, which is important for maintaining laminar flow in applications such as coupling to particle separation devices.

Figure 9:
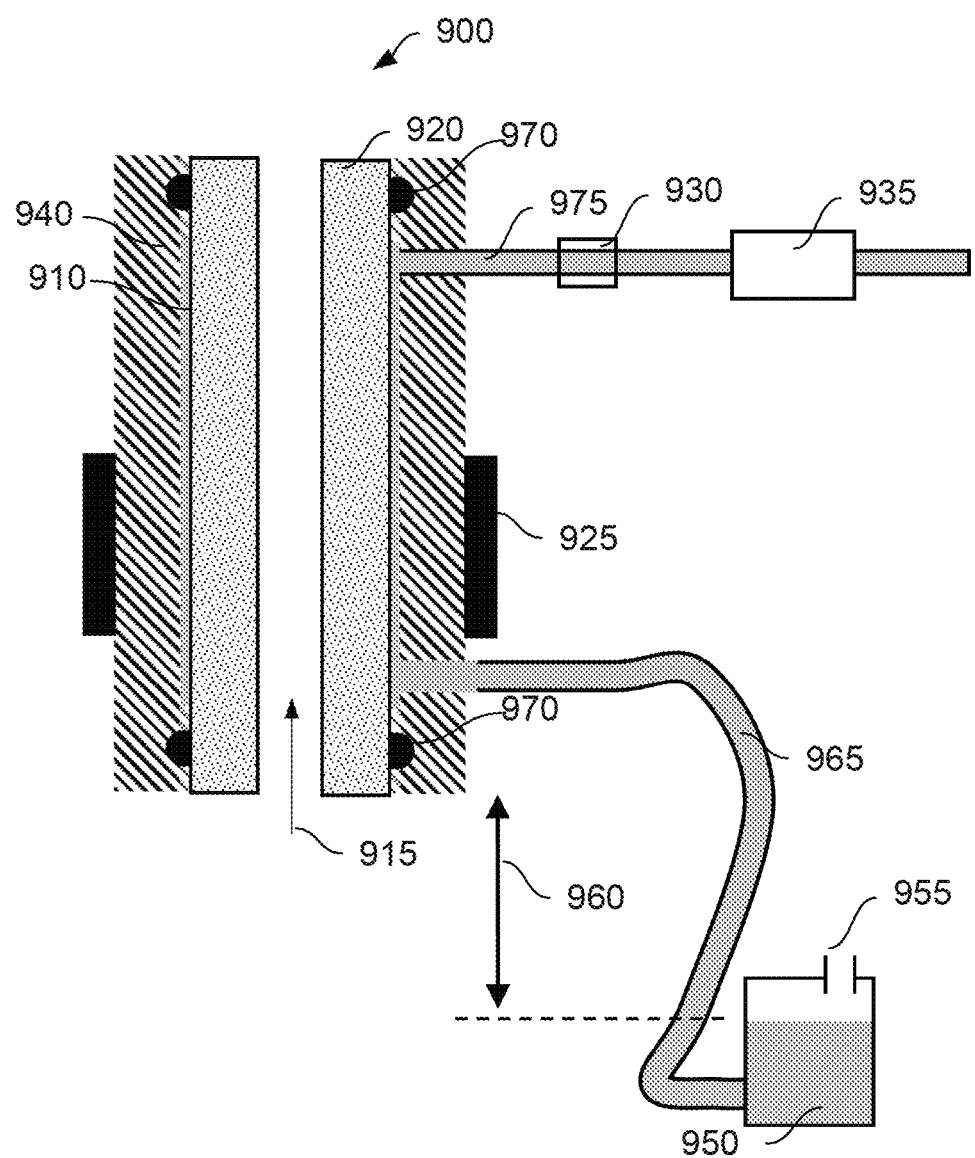
FIG. 9 illustrates an embodiment of the technology comprising a siphoned wick of this technology.

FIG. 9 illustrates an alternative embodiment of the technology comprising a siphoned wick system. Water is drawn up in to a sealed space behind the wick and held at slightly negative pressure. The system includes a housing 940 surrounding a wick 920 with a gap 910 formed between the wick 920 and the housing 940. O-rings 970 at the upper and lower ends of the housing 940 seal water in the gap 910. Water in the gap is fed from a reservoir 950 and feed line 965. A vent 955 is provided on the reservoir 950. A check valve 930 and air purge valve 935 are provided on outlet line 975 from the gap 910. A heater or cooler 925 surrounds the aluminum housing 940.

A system 900 utilizing a water-filled gap 910 behind a wick 920, wherein the water is held at a slightly reduced pressure relative to that of the air flow 915. This pressure difference is less than the bubble point of the wick material, and thus there is no air transport through the wick. Water condensing on a cold wick is immediately pulled through the wick by this negative pressure, where it can then drain into a reservoir 950. Similarly, as water evaporates from a hot wick, replacement water is drawn up from the reservoir 950. Materials that are found to work as a siphoned wick include alumina bisque, or metal fiber filters, such as are available from Beckaert Corp.

Prior to operation, an air purge pump 935 primes the system by pulling air out of the gap 910, causing it to fill with water from the reservoir 950. Alternatively, the system may be primed prior to operation by injecting water directly injected into the gap 910 through one ports 965 or 975. The check valve 930 prevents air from being drawn back into the gap 910, and the pump 935 can then be shut off. In some cases, dissolved air can come out of solution to be trapped, so in some embodiments the pump may be run intermittently or at a low speed to purge bubbles. The hydraulic head of the water in contact with the wick is lower than the altitude 960 of any point on the wick. The slightly negative pressure eliminates the need for the dike of the prior art because any excess water on the wick surface is immediately drawn into the porous material, preventing drips. This action also allows a cold wick to collect condensed water vapor and carry the liquid into the reservoir. The vent 955 is connected to the air flow space 915 to equalize the pressure in the air space of the reservoir.

In another variation, the air-purge pump is replaced by a continuously-running pump, circulating the water in a closed loop. In this variation, the water flow is high enough to carry the necessary heating or cooling power. Instead of controlling the housing temperature, a separate device heats or cools the water itself before it is brought to the wick. In this embodiment, the housing need not be a good thermal conductor. With this approach it is possible to the circulating water stream a means of water filtration, or purification, or removal of soluble gases.

In yet another embodiment, a growth tube may have two or more sections similar to those shown in FIG. 9 at different temperatures. The multiple sections could share a single wick and/or water gap. However, to reduce heat leaks between hot and cold sections, it can be advantageous use separate wicks.

Figure 10:
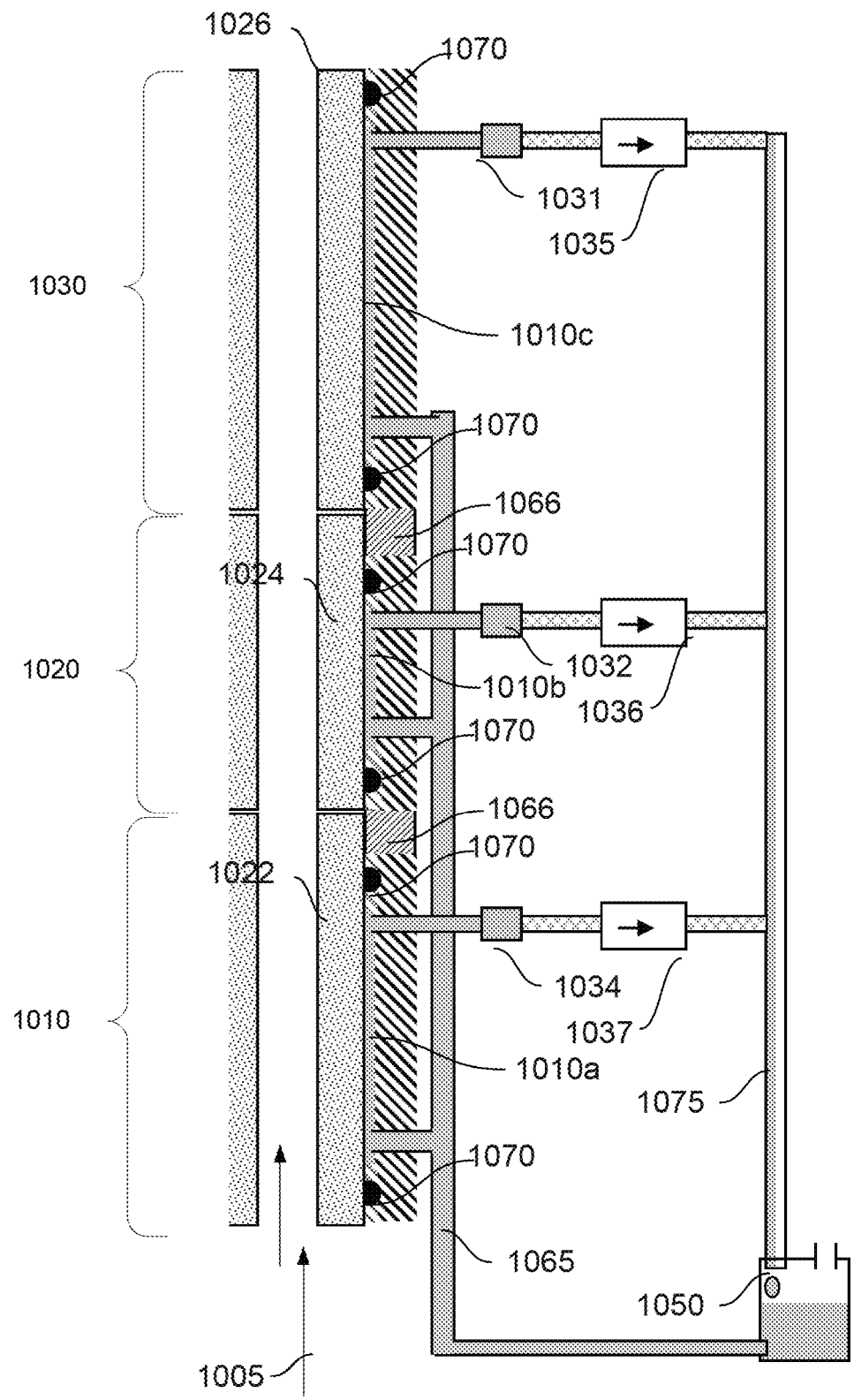
FIG. 10 illustrates an embodiment of the siphon wick system applied to a three-stage condensational growth system.

FIG. 10 shows the siphoned wick concept applied to a system with three wicks sharing a single reservoir. The system includes a housing 1040 surrounding a wick 1022, 1024, 1026 with three gaps 1010a, 1010b and 1010c formed between the wick sections 1022, 1024, 1026 and the housing 1040. O-rings 1070 separate at the upper and lower ends of each section of housing 1040 and seal water in the gaps 1010a, 1010b, and 1010c relative to wick section 1022, 1024, 1026. Water in the gaps is fed from a reservoir 1050 and feed line 1065. A vent 1065 is provided on the reservoir 1050 check valves 1031, 1032, 1034 and air purge valves 1035, 1036 and 1037 are provided on an outlet line 1075 from the gaps 1010a, 1010b, 1010c. The three stages of the system may be operated as a conditioner 1010, the initiator 1020 and equilibrator 1030, with insulators 1066 separating each respective temperature section of the housing 1040.

Despite the negative pressure in the water gap, air is not drawn through the wick to form bubbles in the water. The force preventing this leak is the surface tension of the water adhering to the small pores in the wick. The maximum air pressure a wetted porous material is able to resist is called the "bubble point pressure", given by $$P = \frac{4\gamma k \cos\theta}{d},$$

where
d is the pore size
$\gamma$ is the surface tension of water, $70 \times 10^{-3}$ N/m
$\theta$ is the contact angle between water and the solid, a measure of how hydrophilic the material is;
k is the shape correction factor of order unity, accounts for non-cylindrical pores Surface tension, pore size and contact angle are the same factors that enable capillary action to draw water up into the wick when the bottom end is placed in water reservoir as shown in FIG. 1 in the prior art. Therefore, wick material that is suitable in the prior art is a good candidate for the siphoned wick technology. Note that the siphoned wick method depends on the size of the largest pore in the wicking material and hence a defect in the wick can allow air to bubble into the water gap.

Bubble point pressure is commonly expressed in terms of hydraulic head, the height of a column of water that can be supported by that pressure. The bubble point pressure must exceed the altitude difference between the top of the wick and the water surface in the reservoir. Porous materials are readily available with bubble points in excess of one meter of water, which provides plenty of margin in the height of the device and the altitude of the reservoir.

The siphoned wick method has been implemented using alumina bisque, with the configuration shown in FIG. 10. This implementation has been used to enlarge particles in a parallel plate configuration to enable ultrafine particle counting by optical means. The method has also been applied using as the wick a system constructed from stainless steel fiber filters (Bekipore 3AL3, Beckaert, Marietta, Ga.) welded to a solid stainless steel frame. The Bekipor 3AL3 has a bubble point of about 1 m. This pure stainless construction can be treated with a passivation coating (e.g. Inertium™, AMCX, Tyrone, Pa.) to facilitate the removal of deposited organic material. This latter application is used when enlarging particles to enable collection for chemical analysis while avoiding contamination.

Figure 11:
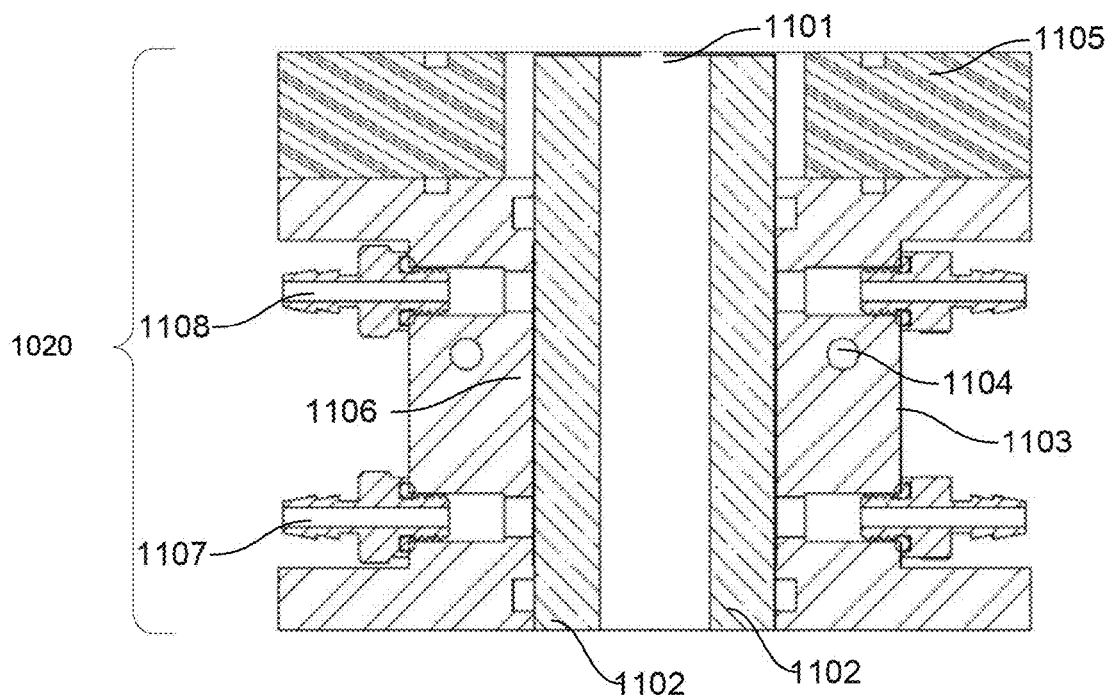
FIG. 11 illustrates an embodiment of the siphon wick system.

FIG. 11 is an enlarged view drawing of the initiator stage 1020 of the three-stage system illustrated in FIG. 10. This is a parallel plate system, wherein the air flows through a 11 mm×60 mm channel 1101. Each wall is lined with 6 mm thick alumina bisque 1102 which serves as the wick. The initiator housing 1103 is constructed of aluminum, which is a good thermal conductor. This is heated by means of cartridge heater 1104. The initiator is isolated from the upstream conditioner section by means of insulator 1105. The wick 1102, is pressed against the housing 1103 by means of clamps located at either end of the channel, not shown in the drawing. A relief in the housing along the central region creates a gap 1106 which is approximately 1 mm deep, and extends most of the length of the initiator. In operation this gap is filled with water, by means of the water inlet ports 1107, and purge ports 1108. The overall length of the initiator and its insulator is about 60 mm. This initiator is 50 mm long, and mates with a 150 mm long conditioner upstream, and a 120 mm long equilibrator downstream. The conditioner stage 1010 and equilibrator section 1030 may be constructed at longer lengths, and are cooled instead of heated, but have the similar wick and wick-wetting features as the initiator. The typical flow rate for this system is around 15 L/min.

The siphoned wick technology illustrated herein offers several engineering advantages. Reservoir level control is provided automatically, while the prior art requires active control of the reservoir level. Surface tension and the typically small length scales can complicate this task in the prior art. For example, refilling can be impacted if the vent gets plugged by a small amount of water. Also, the level sensor can be fooled by an unfortunately located bubble or by tipping the device. These issues are eliminated with the embodiments shown herein. In addition, in systems operating at high temperature or high air flow rate, the viscous pressure drop due to water flowing through the porous medium can become important. In the prior art, large upward transport favors a thick wick, yet good thermal contact between the air and the aluminum favors a thin wick. With the present technology, water is brought to the high altitude by the water-filled gap. A thin wick only makes transport through the wick easier.

Priming is improved in the present technology. Despite having a low (good) contact angle when wet, some materials exhibit a much larger contact angle when completely dry. This can make some otherwise hydrophilic materials "stubborn" to wet initially. In the prior art, water must initially "crawl" up several inches of dry wick. The siphoned wick technology allows use of more difficult-to-wet materials, because the water is actively brought in contact with most of the wick. In addition, in the prior art, the surface of the dike exposed to the air has the potential to degrade the performance. For example, if conditioned (cold) air flows upwards into a growth (hot) section, it will first encounter the warm, dry surface of the dike. The rise in temperature with no added water vapor will reduce the supersaturation that can be achieved. Similarly, in the case of a cold wick, water will tend to condense onto the dike, forming beads that disturb the flow and have the potential to drip. Such situations favor a thick, thermally insulating dike wall. However, minimizing the disturbance of the laminar flow favors a thin dike wall. The present technology, which requires no dike at all allows for an abrupt transition to a new temperature with no dry section and no protrusion into the flow. In addition, in the prior art, making the system robust against flooding would favor a tall dike. However, as mentioned above, time spent inside the non-wetted dike degrades the performance of the growth tube. This is avoided with the present technology.

Thermal conductance between wick and housing is improved with the present technology. The growth tube operation depends on providing heat or cold to the wick, which is improved by good thermal contact with the housing. Thermal contact can be achieved by clamping objects together, but it can be difficult to actively press the wick against the housing. The water-filled gap in the present technology ensures good thermal contact between wick and housing without any mechanical force.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A particle enlargement device, comprising:
   a container into which a flow of particle-laden air is introduced in a laminar manner through in inlet and passes to an outlet, the container having a first section, a second section and a third section though which the particle-laden air flows between the inlet and the outlet, the temperature of the second section is warmer than that of the first section at the inlet and the third section at the outlet, and
   a continuous wick lining an interior wall of each of the first second, second section and third section, said wick being capable of internally transporting liquid water along its length in the first section, second section and third section.

2. The device of claim 1 wherein the interior wall of the first section, second section and third section defines at least one cylindrical channel.

3. The device of claim 1 wherein each section includes a plurality of interior cylindrical channels, each channel defined by an interior wall and being lined with a channel wick comprising a portion of the continuous wick.

4. The device of claim 1 wherein the first section, second section and third section include one or more parallel plates, each parallel channel lined with a continuous wick along each interior wall.

5. The device of claim 1 wherein the temperature of the second section is at least 20° C. warmer than the first section.

6. The device of claim 1 further including a water inlet coupled to the second section and a portion of the wick in the second section.

7. The device of claim 1 further including a fluted portion of the container at the inlet or outlet, and positioned to receive excess fluid from the continuous wick.

8. The device of claim 1 further including a preconditioner provided at the inlet.

9. The device of claim 8 wherein the preconditioner is a nafion tube though which the particle laden flow passes prior to entering the inlet.

10. The device of claim 8 wherein a portion of particle laden flow from the outlet is returned to the preconditioner and used to condition the particle laden air entering the inlet.

11. A method of particle enlargement in a container, comprising:
    providing a container into which a particle laden flow may be introduced, the container having flow region defined by an interior wall having a first region, a second region and a third region, and a continuous wick positioned along the interior wall in each of the first region, second region and third region;
    introducing the particle laden flow into the container in a laminar manner;
    operating the first region of the container at a first temperature, the second region of the container at a second temperature and the third region of the container at a third temperature, the second temperature higher than the first and third temperatures.

12. The method of claim 11 further including regulating the temperature of the third section is regulated based on measurement of input conditions to produce output flow with water content equivalent to water content in the particle laden flow introduced into the container.

13. The method of claim 11 wherein the second temperature is at least 20° C. warmer than the first temperature.

14. The method of claim 11 further including providing water into the wick and wherein said operating comprises selecting the first temperature, second temperature and third temperature, and a flow rate of the particle laden flow, such that continuous particle enlargement operation is provided in the container with said water stored in and recovered by condensation in the third stage.

15. The method of claim 11 wherein the third temperature is regulated based on measurement of input conditions to produce output flow with the same water content as the introduced air flow.

16. The method of claim 11 further including injecting water into the second section.

17. The method of claim 16 further providing a fluted section of the container and wherein excess liquid water is removed by suction on the fluted section.

18. The method of claim 11 further including preconditioning the particle laden flow to include moisture content based on an output of the container.

19. The method of claim 18 further including returning a portion of the output to a preconditioner through which the particle laden flow passes prior to entering the container.

* * * * *